United States Patent [19]

Saliaris

[11] 4,108,181

[45] Aug. 22, 1978

[54] CAUTERY DEVICE FOR OPHTHALMIC OR THE LIKE SURGICAL APPLICATION

[75] Inventor: George P. Saliaris, Worthington, Ohio

[73] Assignee: Unicare Systems, Inc., Columbus, Ohio

[21] Appl. No.: 763,580

[22] Filed: Jan. 28, 1977

[51] Int. Cl.² .............................................. A61B 17/38
[52] U.S. Cl. .................................. 128/303.1; 30/140; 219/233; 219/240; 228/51
[58] Field of Search ........... 128/303.1, 303.13, 303.14, 128/303.17, 303.18, 405; 219/221, 227–241, 268; 200/60; 30/140; 240/10.66; 228/51–55

[56] References Cited

U.S. PATENT DOCUMENTS

| 2,030,285 | 2/1936 | Dinyer ....................... 128/303.14 X |
| 2,619,576 | 11/1952 | Greibach ............................. 219/240 |
| 3,234,356 | 2/1966 | Babh ........................ 128/303.14 X |
| 3,295,514 | 1/1967 | Hein et al. ...................... 219/233 X |
| 3,613,682 | 10/1971 | Naylor ............................. 128/303.1 |
| 3,662,151 | 5/1972 | Haffey ....................... 128/303.14 X |
| 3,691,342 | 9/1972 | Giles et al. ........................ 219/233 |
| 3,742,187 | 6/1973 | Folus ................................. 219/240 |
| 3,978,312 | 8/1976 | Barton et al. .................... 219/240 |

FOREIGN PATENT DOCUMENTS

| 187,380 | 10/1956 | Austria ................................... 219/233 |
| 668,561 | 8/1965 | Belgium ................................. 219/233 |
| 852,667 | 2/1940 | France ................................... 219/233 |
| 1,188,835 | 9/1959 | France ................................... 219/233 |
| 462,317 | 3/1937 | United Kingdom ..................... 219/268 |

Primary Examiner—Lee S. Cohen
Attorney, Agent, or Firm—Hopgood, Calimafde, Kalil, Blaustein & Lieberman

[57] ABSTRACT

The invention contemplates a disposable, self-contained, battery-operated cautery featuring a finger-grasping end which is of substantially reduced diameter as compared with the battery-containing body portion of the device. Such reduced finger-grasping proportions enable facile and precise manipulation of a cauterizing tip, and a switch actuator carried at the finger-grasping end further facilitates manipulation. The switch actuator is of such low profile as to be fully encased and protected when a protective cover is telescopically assembled over the tip end of the cautery.

12 Claims, 5 Drawing Figures

CAUTERY DEVICE FOR OPHTHALMIC OR THE LIKE SURGICAL APPLICATION

This invention relates to disposable, self-contained, battery-operated cautery devices, of the kind used in ophthalmic surgery.

Prior devices of the character indicated are typified by the showing of U.S. Pat. No. 3,613,682, wherein a heated-wire electrode tip projects beyond an end of a tubular housing that is large enough to contain the battery or batteries needed in operation. A switch actuator projects outside the battery housing near the tip end, and a removable closure cap must be telescoped over the end of the battery housing into locked engagement with the switch actuator, in order to avoid inadvertent actuation of the switch. It is of utmost importance to avoid switch actuation due to the extremely short useful life of the cautery, generally a matter of minutes, and of course the surgeon places great reliance upon the instant readiness of the cautery for its intended, highly delicate purpose. The finger-gripped diameter of such prior devices has impaired and limited surgical manipulation, and the readiness with which a switch-locked position can be dislodged is a constant source of surgeon distrust in the efficacy of the particular cautery he happens to pick up for immediate use.

It is accordingly an object of the invention to provide an improved device of the character indicated.

Another object is to provide such a device with vastly superior manipulative capability and with inherently improved safeguarding against inadvertent operation.

A further object is to meet the above objects with structure providing improved protection of heater tip and switch elements.

It is also an object to meet the above objects with simpler structure, featuring subassemblies which are readily assembled to complete the cautery and which assure surgeon confidence through repeatable reliable operation, from one to the next of a succession of mass-produced disposable cauteries.

Other aspects and various further features of novelty and invention will be pointed out or will occur to those skilled in the art from a reading of the following specification in conjunction with the accompanying drawings. In said drawings, which show, for illustrative purposes only, a preferred form of the invention:

Figure 1:
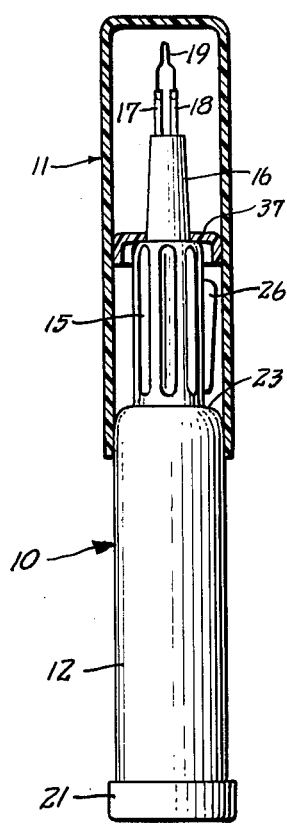
FIG. 1 is a view in elevation of a cautery of the invention, with a removable closure cap in place but shown in longitudinal section.

The invention is shown in application to a cautery comprising a manually manipulable body 10 and a removable protective closure cap 11, both of insulating plastic construction. The base end 12 of the body is enlarged and tubular, defining a cavity 13 for axial reception and housing of a standard dry-cell battery 14, for example a 1.5-volt cell, of size AA. The upper end of the body is first reduced at a finger-grasping portion 15; it is then further reduced at a tip support 16. Two spaced parallel electrodes 17–18 are embedded in the tip support 16, and a suitably formed heater-wire tip 19, as of nichrome wire, connects the projecting ends of the electrodes. Within the battery housing 12, a spring 20 of conductive metal is compressionally loaded by a bottom-closure cap 21 into electrical contact with the base or negative pole of battery 14, and the positive pole 22 is in turn compressionally loaded into electrical contact with the downwardly projecting end of electrode 17. To assure precise frictional retention of cap 21 on battery housing 12, a raised central part of the inner surface of the closed end of cap 21 is sized for centering location of the lower end of spring 20.

In accordance with one feature of the invention, the cautery body portions 12–15 are, together, a single injection-molded part, integrally connected at a relatively sharply defined shoulder 23 and defining a reduced cavity 24 within the finger-grasping portion 15. An elongate angularly localized opening 25 is formed in the reduced tubular portion 15 for movable reception of a switch actuator 26, and the spaced downwardly projecting ends of electrodes 17–18 are received in the reduced cavity 24. An elongate stiffly compliant strip 27 of conductive metal extends from a spring contacting lower end 28 to an upper or forward end 29 in normally offset but potentially contacting relation to the lower end of electrode 18. Strip 27 includes at least one bend in the region of its longitudinal overlap with battery 14, thereby affording a resiliently loaded positioning of battery 14 against that part of the cavity wall 13 which is diametrically opposite strip 27. The actuator 26 is preferably channel-shaped and of channel-bottom width to assure aligned subassembly to strip 27 at upper end 29, such subassembly being shown by permanent thermal deformation of anchoring projections 30 through spaced openings in end 29, as best seen in FIG. 4.

Figure 2:
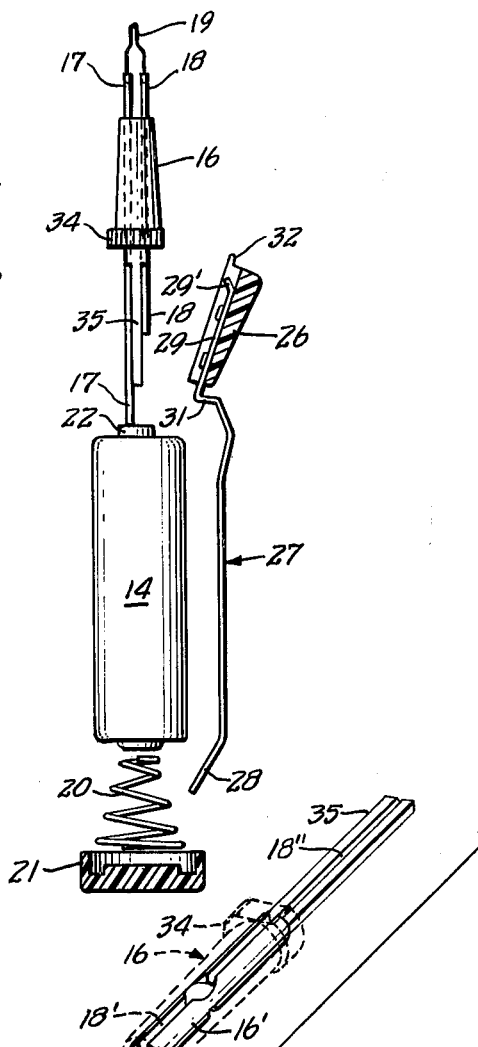
FIG. 2 is a simplified exploded view of some of the parts and subassemblies of the cautery of FIG. 1, but with housing and closure parts removed.
Figure 3:
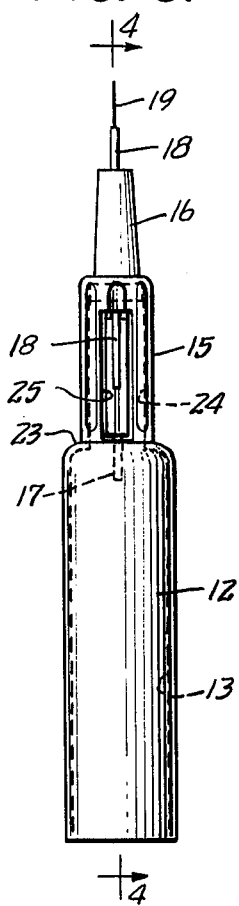
FIG. 3 is a view similar to FIG. 1, but taken of the right-side aspect, and taken only for the housing body parts in partially assembled relation.

In FIG. 2, the compliant strip 27 is shown in its unassembled, unstressed state. It has multiple bends including two closely adjacent substantially right-angle bends defining an offset 31, for axial location within chamber 13 and against the inner wall of the housing shoulder 23. The effective unstressed longitudinal span $D_1$ between offset 31 and the lower end of the strip at 28 is preferably in excess of the inside longitudinal span between shoulder 23 and the bottom of battery housing 12, when closed by cap 21. Such a relationship assures that strip 27 will be resiliently loaded in its axial reaction to and between shoulder 23 and cap 21, thus longitudinally stabilizing the location of actuator 26. As shown, the upper tip end 29' of strip 27 is radially inwardly bent for clean and sharply biting contact with electrode 18. Preferably, the forward end of actuator 26 has small integral lug projections 32 to engage under the adjacent forward lip of access opening 25 (to define a normal radially outer limit of positioning for actuator 26), and the substantially larger remainder of the forward end of actuator 26 is preferably spaced a distance $D_2$ beyond offset 31, which distance $D_2$ is slightly less than the span $D_3$ between the locating surface of shoulder 23 and the forward lip of access opening 25. Finally, the effective length $D_4$ and width of actuator 26 should be such as to allow clearance relation with the corresponding length ($D_5$) and width dimensions of the access opening 25, this operating clearance being maintained at all times, and the relative longitudinal position being assured by the resiliently loaded reference of offset 31 to shoulder 23.

In accordance with a further feature of the invention, the electrode or tip-support body member 16 constitutes, with electrodes 17–18 and tip 19, a further subassembly for unitary force-fit assembly to the housing body portion 15. As shown, the forwardly projecting end of member 16 is tapered, with gentle convergence toward tip 19. Member 16 includes a ribbed circumferential flange 34 at the large end of the taper of its body, and an integrally formed tail 35 extends downwardly in space-retaining contact with and between overlapped lower regions of electrodes 17–18. Support member 16 may be a single-piece injection-mold plastic part complete with tail 35 and two elongate passages, for force-fitted reception of the electrodes 17–18; however in its preferred form (see FIG. 5), the support member 16 comprises two injection-molded plastic parts, namely, an outer sleeve part (phantom outline in FIG. 5) having the tapered and flange (34) external formations already discussed, and a central core part 16' integral with tail 35 and longitudinally grooved at diametrically opposed locations 17'-18' to receive and anchor the electrodes 17–18 prior to pressfitted assembly to the bore of said sleeve. Once thus assembled to its electrodes (and tip 19), support 16 is further assembled to the tubular housing by insertion through the lower open end of housing portion 12, with force-fitted permanent retention at flange 34 within housing portion 15 and in axially locating abutment with an end flange formation 36 at the upper end of the finger-grip housing portion 15 (see FIG. 4). In such location, the shorter electrode 18 is near opening 25 and the longer electrode 17 is relatively remote from opening 25, as will be understood. Preferably, the lower end of tail 35 extends substantially to the lower end of access opening 25.

Figures 4, 5:
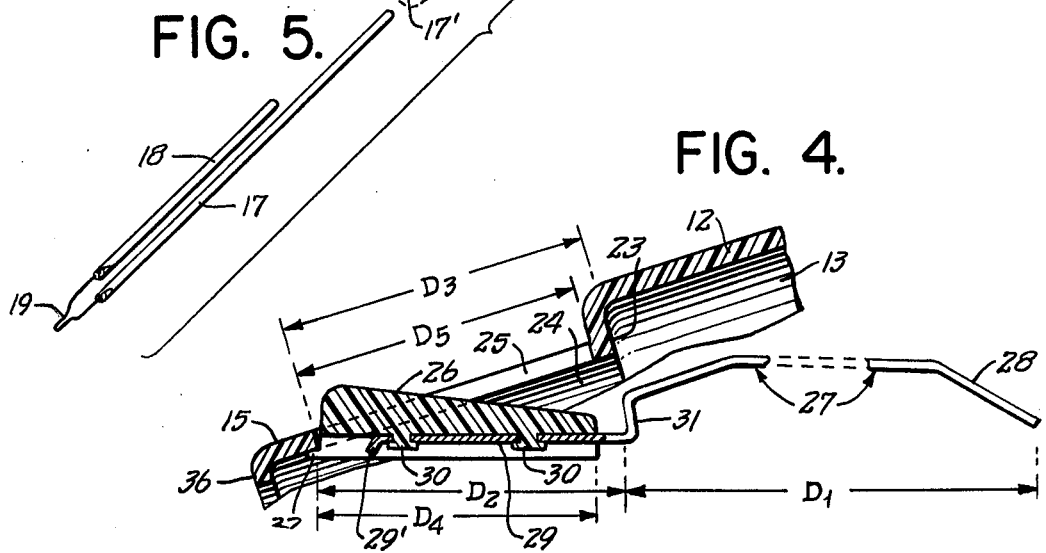
FIG. 4 is an enlarged fragmentary longitudinal sectional view to show electric-switch parts in relation to housing parts, the section in the same aspect plane as designated 4—4 in FIG. 3.
FIG. 5 is an exploded view in perspective to reveal detail of one of the subassemblies of FIG. 2.

To assemble the described cautery, and assuming that support body 16 and its electrode and tip structure have been fitted to the tubular body portion 15, the switch subassembly 26–27 is inserted through the lower end of battery-housing portion 12, until actuator 26 locates in opening 25, generally in conformity with FIG. 4. The bent end 28 of strip 27 is then finger-deflected, to permit insertion of battery 14 alongside strip 27. The bent end 28 will then temporarily hold battery 14 against loss and until spring 20 and cap 21 are set in place, at which time battery 14 will have assumed its preloaded contact with electrode 17, and actuator 26 is poised for use, having the elevational profile shown in FIG. 1, i.e., well within the longitudinal geometric projection of battery housing 12. A cupped flange or washer member 37 is then selected, with a central opening sized for frictional yet removable retention by and upon assembly (over tip 19) to the large end of the taper of support member 16; the cupped or washer member 37 is also selected for its relatively strong interference-fit relation to the bore of closure cap 11, so that upon assembly of cap 11 over washer 37, and upon further cap 11 pressure to the point of telescoping overlap with batteryhousing portion 12, as shown in FIG. 1 (and as for example until washer 37 abuts a stop or lug, not shown, molded into the bore of cap 11), washer 37 will have become a permanently inserted stop or locating part of cap 11. Cap 11 in its removable assembly to cautery 10 is positively centered by washer 37 at shoulder 36, and it is stablized against angular dislocation by reason of the telescopic fit to battery housing 12. At the same time, actuator 26, in its normal outwardly retained position (FIG. 1) remains in safe clearance within the protective and ensheathing bore of cap 11. When the cautery must be readied for use, cap removal is centrally piloted by washer 37 along support body 16, assuring maximum protection of tip 19 and actuator 26 against contact. In use, the surgeon establishes ready grip of the reduced body portion 15 between his thumb and middle finger, affording convenient index-finger depression of actuator 26 whenever tip 19 must be heated. For the described form, wherein a size AA 1.5-volt battery is caused to excite a 10-mil nichrome wire tip, a cauterizing-tip temperature of 1200 ± 100° F. is reached in less than 5 seconds.

The described embodiment of the invention will be seen to have achieved all stated objects. The provision of a reduced finger-grip portion achieves maximum response to manipulation, and the provision of switch control on this reduced portion, convenient for index-finger operation, affords even greater response to allow the surgeon's individual dexterity its maximum application to the job at hand. The device of the invention well serves such demanding and space-limited applications as ophthalmalogical surgery, within the eyeball itself.

While the invention has been described in detail for the preferred form shown, it will be understood that modifications may be made without departure from the scope of the invention.

What is claimed is:

1. A disposable, self-contained cautery comprising an elongate tubular housing defining a battery-holder cavity at a base end and a reduced cavity at a finger-grip end which forwardly projects for said base end, said reduced cavity being of lesser diametral proportions than said battery-holder cavity and the end of said battery-holder cavity opposite said finger-grip end being closed, there being an interior generally radial shoulder formation in the inner surface of said housing at the juncture of said base and finger-grip ends, first and second spaced electrodes carried at a forward end of said finger-grip end opposite said base end and projecting longitudinally beyond said forward end, a heater-wire tip connecting the forwardly projecting ends of said electrodes and projecting forwardly thereof, one of said electrodes extending a first distance within said housing to the battery-holder cavity for contact with the forward terminal of an inserted battery, the other of said electrodes extending within said finger-grip end and for a distance less than said first distance, said finger-grip end of said housing having a switch-access opening local to the angular region of adjacency to said other electrode, and a switch subassembly comprising an elongate longitudinally extending stiffly compliant metal strip with an insulating finger-engageable actuator element secured to one side of said strip at one end thereof, said actuator element being radially positioned and movable within said access opening and said strip having relatively close and opposite substantially right-angle bends near said actuator element to define a radially outward offset in axially forward locating abutment with said shoulder, and means at the closed end of said battery-holder cavity providing an axially rearward locating abutment for the other end of said strip and electrically conductive connection of said strip to the rear terminal of an inserted battery, thereby controlling the positioning of said actuator element in said access opening.

2. The cautery of claim 1, in which said actuator element and the access-opening region of said housing include coacting formations limiting the radially outward movement of said actuator element said strip in unstressed condition being so formed that when in said housing and located at said shoulder said strip is normally urged out of contact with said other electrode and to the limiting displacement position established by coaction of said limiting formations.

3. The cautery of claim 2, in which said actuator element in said limiting displacement position is contained within the longitudinal geometrical projection of the base end of said housing, and a tubular protective cover extending over said tip and over the finger-grip end of said cautery and having removable telescoping engagement with said base end of said housing, whereby placement of said cover affords full protection of said tip and a safeguard against switch-actuating access.

4. The cautery of claim 1, in which said forward end of said finger-grip end terminates at a reduced opening defined by a radially inward flange formation, and in which said electrodes and tip are parts of a subassembly including an insulating body in which corresponding intermediate lengths of said electrodes are embedded, said body having a gently tapered forwardly projecting tip-supporting end extending through said reduced opening and a radially outward flange formation located within said finger-grip housing end and axially against said radially inward flange formation.

5. The cautery of claim 4, in which said body further includes an integral elongate tail portion between and in spacing contact with said electrodes for at least the region of axial overlap of said electrodes within said housing.

6. The cautery of claim 5, in which said tail portion extends longitudinally away from said body flange portion for at least the distance of axial overlap with said actuator element.

7. The cautery of claim 5, in which said tail portion extends longitudinally away from said body flange portion for substantially the axial distance to said shoulder.

8. The cautery of claim 4, in which said body comprises an elongate sleeve part having a cylindrical bore, and a cylindrical core part secured to said bore, said core part having elongate diametrically opposed grooves, each groove locating and retaining one of said electrodes.

9. The cautery of claim 8, in which said core part further includes an integral elongate tail portion between said electrodes and extending rearwardly of the region of the sleeve part, at least part of said tail portion being between said electrodes to maintain at least the groove-located separation of said electrodes.

10. The cautery of claim 1, in which a closure member removably closes the closed end of said battery-holder cavity, said strip extending into locating abutment with said closure member when said radially outward offset is in locating abutment with said shoulder.

11. The cautery of claim 1, in which said strip has at least one bend within the unstressed longitudinal span of said strip from said offset to said other end, and in which said span exceeds the inside longitudinal span between said shoulder and the closed end of said battery-holder cavity, whereby said strip is compressionally preloaded into its shoulder-located position.

12. A disposable self-contained cautery comprising an elongate tubular housing body defining a battery-holder cavity at a base-end portion and having a reduced forwardly projecting finger-grip portion adjacent one end of said battery-holder cavity, said reduced portion being of lesser diametral proportions than said battery-holder cavity, said housing body further including an insulating tip support extending forwardly of said finger-grip portion, said tip support being further reduced with respect to said finger-grip portion and defining with the forwardly projecting end of said finger-grip portion a radial shoulder, said tip support tapering inwardly in the forwardly projecting direction, a heater-wire tip projecting forwardly of the forwardly projecting end of said tip support, battery and switch conductor means carried by and within said housing body for selective excitation of said tip, said means including an externally accessible switch actuator movably carried at one angular location on said finger-grip portion, said switch actuator having a normal switch-open position within the longitudinal geometrical projection of said base-end portion, and a tubular closure cover extending over said tip, tip support and finger-grip portion and having removable telescoping fit over said base-end portion, said cover including a longitudinally central radially inward flange having frictional retaining engagement with the taper of said support when said cover flange is axially located adjacent said shoulder, whereby positive cover positioning is established close to the region of tip support and further whereby the telescoped engagement with said base-end portion stabilizes said cover against angular misalignment with respect to the housing-body axis.

* * * * *